US00PP37792P2

(12) United States Plant Patent
Couturieux

(10) Patent No.: US PP37,792 P2
(45) Date of Patent: Oct. 20, 2026

(54) ***HYDRANGEA* PLANT NAMED 'Coubell'**

(50) Latin Name: *Hydrangea paniculata*
Varietal Denomination: Coubell

(71) Applicant: Breederplants VOF, Gouda (NL)

(72) Inventor: Jacques Couturieux, Moyenmoutier (FR)

(73) Assignee: Breederplants VOF, Gouda (NL)

( * ) Notice: Subject to any disclaimer, the term of this patent is extended or adjusted under 35 U.S.C. 154(b) by 0 days.

(21) Appl. No.: 19/379,020

(22) Filed: Nov. 4, 2025

(51) Int. Cl.
*A01H 5/02* (2018.01)
*A01H 6/48* (2018.01)

(52) U.S. Cl.
USPC ..... Plt./250

(58) Field of Classification Search
USPC ..... Plt./250
CPC ..... A01H 5/00; A01H 5/02; A01H 6/48
See application file for complete search history.

(56) References Cited

U.S. PATENT DOCUMENTS

PP33,877 P2 * 1/2022 Rouwette ..... Plt./250

OTHER PUBLICATIONS

Breederplants Product range, retrieved on Feb. 23, 2026 at https://breederplants.nl/en/hydrangea-paniculata-coubell-white-a-bella, 5 pp. (Year: 2026).*

* cited by examiner

*Primary Examiner* — June Hwu
(74) *Attorney, Agent, or Firm* — Weatherly IP Solutions, LLC; Karen P. Bechtold; James M. Weatherly

(57) ABSTRACT

A new *Hydrangea* plant named 'Coubell' particularly distinguished by globe-shaped flowers, strong stems, and large dark-green leaves, is disclosed.

3 Drawing Sheets

Genus and species: *Hydrangea paniculata.*
Variety denomination: 'Coubell'.

BACKGROUND OF THE NEW PLANT

The present invention comprises a new and distinct variety of *Hydrangea* plant, botanically known as *Hydrangea paniculata*, and hereinafter referred to by the variety name 'Coubell'. 'Coubell' originated from an open pollination in 2015 using female parent 'Grandiflora' (not patented) and an unknown male parent in Moyenmotier, France. Seeds from the open-pollination were selected in August 2018 in Moyenmotier, France.

'Coubell' was first propagated in July 2021 in Moyenmotier, France by softwood cuttings. 'Coubell' was found to reproduce true to type in successive generations of asexual propagation via softwood cuttings.

SUMMARY

The following are the most outstanding and distinguishing characteristics of this new variety when grown under normal horticultural practices in Boskoop, The Netherlands.

2. Globe shaped flowers;
3. Strong stems; and
4. Large dark-green leaves

DESCRIPTION OF THE PHOTOGRAPHS

This new *Hydrangea* plant is illustrated by the accompanying photographs which shows the plant's overall plant habit including form, and foliage. Photos were taken of 20-month-old plants in September 2025 in Boskoop, Netherlands. The colors shown are as true as can be reasonably obtained by conventional photographic procedures.

Figure 1:
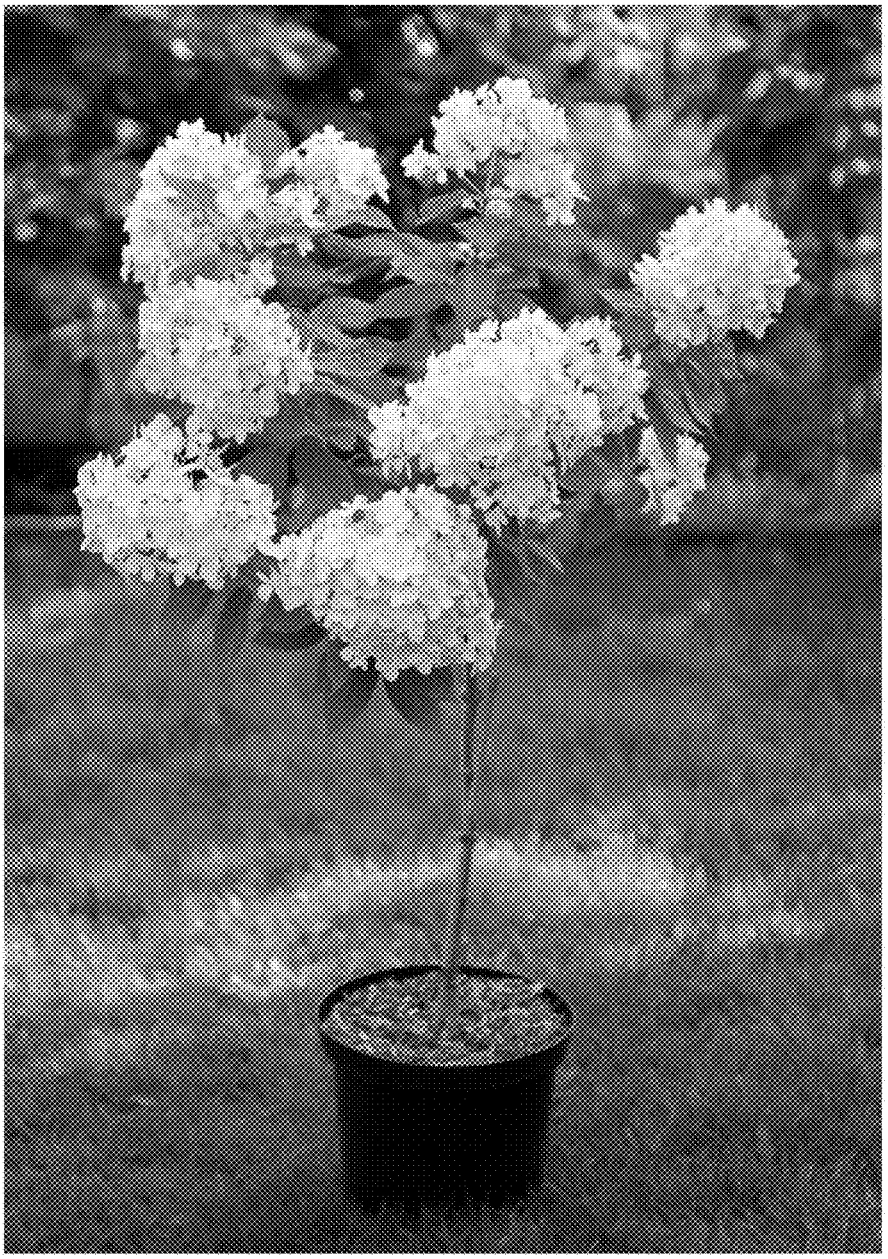
Figure 2:
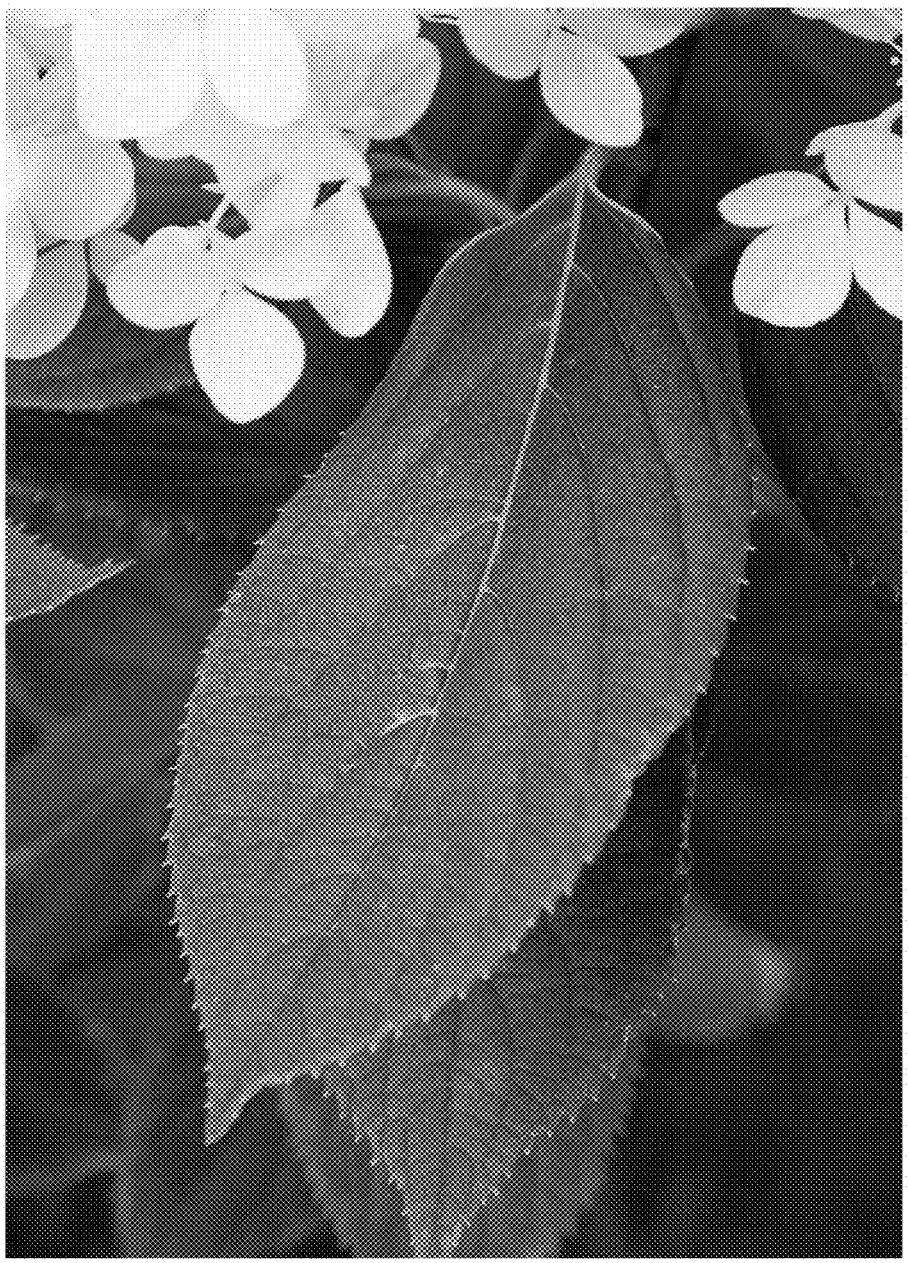
Figure 3:
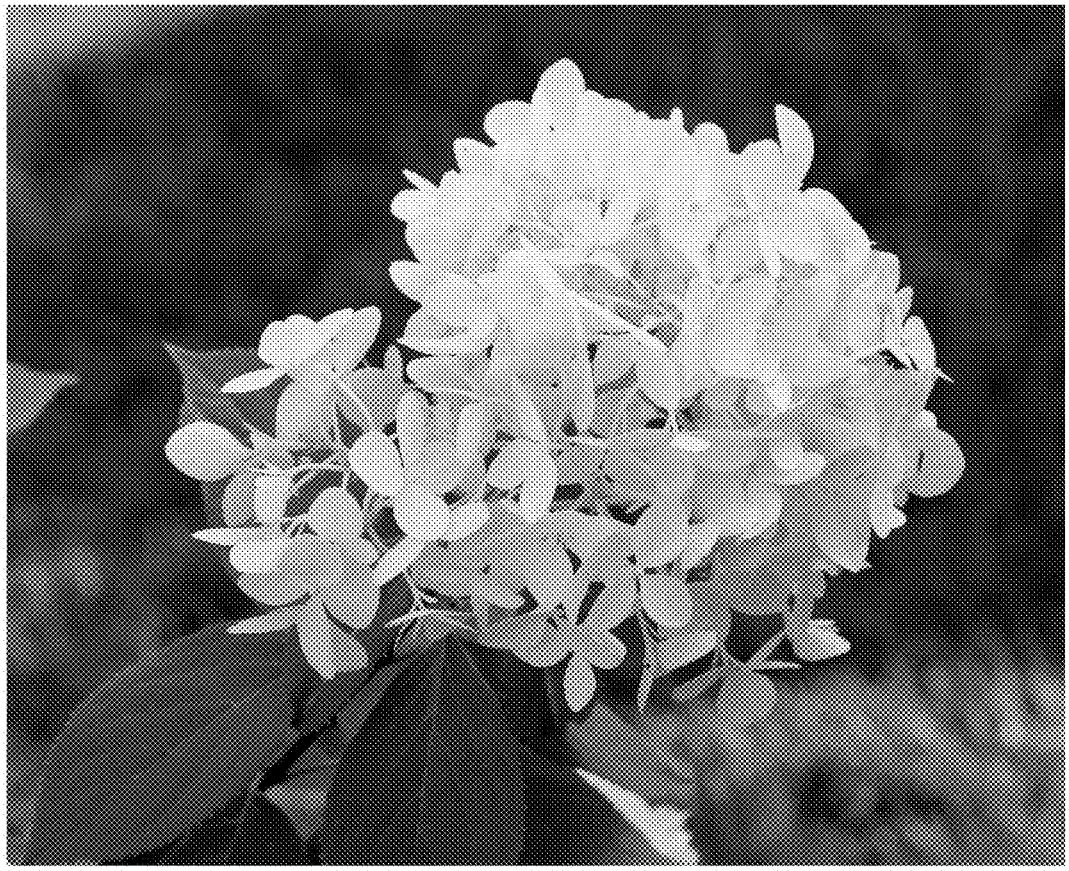

FIG. 1 shows the 20-month-old plant of 'Coubell'.
FIG. 2 shows a close-up of the foliage.
FIG. 3 shows a close-up of the inflorescence.

DESCRIPTION OF THE NEW VARIETY

The following detailed descriptions set forth the distinctive characteristics of 'Coubell'. The data which define these characteristics were collected from asexual reproductions carried out in Boskoop, Netherlands. Data was collected on 20-month-old plants grown outdoors in 50 cm circular containers in Boskoop, Netherlands in September 2025. Color references are to The R.H.S. Colour Chart of The Royal Horticultural Society of London (R.H.S.), 6$^{th}$ edition (2019 reprint).

Classification:
*Family.*—Hydrangeaceae.
*Botanical.—Hydrangea paniculata.*
*Common.—Hydrangea.*
*Designation.*—'Coubell'.

Parentage:
*Female parent.*—'Grandiflora' (not patented).
*Male parent.*—Unknown.

Propagation:
*Type.*—Cuttings and grafting.
*Time to produce a rooted young plant.*—January by grafting and June, July and August by cuttings.
*Root description.*—Non-fleshy, slightly fibrous, colored yellow-white; RHS 158A and 158B.
*Rooting habit.*—Moderately branched, moderately dense.

Plant:

*Growth habit.*—Broad spreading-upright.

*Shape.*—Flattened globular.

*Average height.*—54.5 cm.

*Average plant spread.*—80.5 cm.

*Plant vigor.*—Moderate.

Branches:

*Habit.*—Moderately free branching.

*Number of branches.*—Average: 14.

*Shape.*—Rounded.

*Color.*—Immature: RHS 145D (Yellow-green), fading to RHS 199A and RHS 199B (Grey-brown). Mature: A blend of RHS 197A, RHS 199A and RHS N199A (Greyed-green to grey-brown).

*Average length.*—Average: 36.3 cm.

*Average width.*—Average: 0.4 cm.

*Strength.*—Strong.

*Texture.*—Smooth, glabrous, except for immature branches; moderately covered with very short adpressed hairs, average length: 0.5 mm, colored close to RHS 145D (yellow- green).

*Average internode length.*—2.8 cm.

Foliage:

*Leaf arrangement.*—Opposite.

*Shape.*—Ovate to elliptic.

*Average length.*—11.7 cm.

*Average width.*—6.3 cm.

*Apex.*—Apiculate.

*Base.*—Short attenuate.

*Margin.*—Serrulate.

*Texture.*—Upper surface: Sparsely covered with very short, adpressed hairs, average length: 0.5 mm. Lower surface: Sparsely to moderately covered with very short, adpressed hairs, average length: 0.75 mm.

*Color.*—Young Foliage: Upper Surface: RHS 143A (Green). Lower surface: RHS 146B (Yellow-green). Mature Foliage: Upper Surface: RHS 137B (Green). Lower surface: A blend of RHS 146B and RHS 147B (Yellow-green). Venation: Type: Pinnate. Color Young Foliage: Upper Surface: RHS 144B (Yellow-green). Lower surface: RHS 145C (Yellow-green). Mature Foliage: Upper Surface: RHS 144A to 144B (Yellow-green). Lower surface: RHS 145C (Yellow-green). Petiole: Average Length: 2.1 cm. Average Width: 0.3 cm. Color: Upper Surface: RHS N148B (Yellow-green), tinged with RHS N199B (Grey-brown). Lower surface: RHS 146C (Yellow-green). Texture: Upper Surface: Sparsely to moderately covered with very short, adpressed hairs, average length: 0.5 mm and shorter. Lower surface: Smooth, glabrous.

Inflorescence:

*Natural flowering season.*—Summer to late summer.

*Inflorescence type.*—Panicle.

*Lastingness.*—Approximately 5 weeks.

*Conspicuousness of fertile flowers.*—Low.

*Panicle.*—Shape: Flattened globular. Average Height: 17.5 cm.

*Average diameter.*—19.5 cm.

*Fragrance.*—Faint, sweet and pleasant.

*Sterile flowers.*—Flowers per inflorescence: Average of 160. Aspect: Upward to outward and slightly drooping. Shape: Rotate to cruciform. Average Length: 1.0 cm. Average Diameter: 3.9 cm. Persistence: Persistent. Bud: Average Length: 0.5 cm. Average Diameter: 1.1 cm. Shape: Broad cup-shaped. Color: RHS 145B (Yellow-green). Petals: Number: Average: 4. Arrangement: Cruciform. Shape: Ovate, concave. Tip: Acute. Base: Cuneate. Margin: Entire. Average Length: 0.4 cm. Average Width: 0.2 cm. Texture: Upper surface: Smooth, glabrous. Lower surface: Smooth, glabrous. Color: Upper Surface: RHS NN155A, fading to RHS 155C towards the tip (White). Lower Surface: RHS NN155A, fading to RHS 155C towards the tip (White). Sepals: Number: Average: 4, occasionally 3. Arrangement: Cruciform (if 4 sepals), occasionally rotate (if 3 sepals). Shape: Elliptic to obovate. Tip: Broad acute to broad bluntly acute. Base: Attenuate. Margin: Entire. Average Length: 2.2 cm. Average Width: 1.6 cm. Texture Upper surface: Smooth, glabrous. Lower surface: Smooth, glabrous. Color: Beginning to open: Upper surface: RHS NN155A (White). Lower surface: RHS NN155A (White). Fully Opened: Upper surface: RHS 155A (White) fading to RHS 145B and RHS 145C (Yellow-green). Lower surface: RHS 155A (White) fading to RHS 145C and RHS 148D (Yellow-green).

*Pedicel.*—Length: Average: 2.4 cm. Diameter: Average: 0.1 cm. Strength: Strong. Texture: Moderately covered with very short adpressed hairs, average length: 0.3 mm and shorter. Color: RHS 157C and 157D (Green-white).

*Fertile flowers.*—Flowers per inflorescence: Average: 75. Aspect: Upward to slantly outward. Shape: Rotate. Length: Average: 0.5 cm. Diameter: Average: 1.0 cm.

*Bud.*—Length: Average: 0.4 cm. Diameter: Average: 0.3 cm. Bud shape: Broad obovate. Bud color: RHS 155C (White); immature calyx is RHS 157A (Green-white).

*Petals.*—Number per flower: Average: 5. Arrangement: Rotate. Shape: Ovate. Tip: Acute. Base: Cuneate. Margin: Entire. Length: Average: 0.35 cm. Width: Average: 0.2 cm. Texture Upper Surface: Smooth, glabrous. Lower surface: Smooth, glabrous. Color: Upper surface: RHS NN155A, fading 155C towards the tip (White). Lower surface: RHS NN155A, fading 155C towards the tip (White).

*Fertile flower sepals.*—Number per flower: Average: 5. Arrangement: Rotate. Shape: Deltoid, base fused. Tip: Acuminate. Base: Cuneate, fused. Margin: Entire. Length: Average: 1.25 cm. Width: Average: 1.0 m. Texture: Upper Surface: Smooth, glabrous. Lower surface: Smooth, glabrous. Color: Upper surface: RHS 145D (Yellow-green). Lower surface: RHS 145D (Yellow-green).

*Fertile flower pedicel.*—Length: Average: 1.0 mm. Diameter: Average: 0.5 mm. Strength: Strong. Texture: Moderately covered with very short adpressed hairs, average length: 0.2 mm and shorter. Color: A blend of RHS 145D and RHS 150D (Yellow-green).

Reproductive organs:

*Sterile flower.*—Stamens: Number: Average 10. Filament length: Average: 0.4 cm. Filament color: RHS NN155D (White). Anthers: Shape: Short oblong. Length: Average: 0.1 cm. Color: Lighter than RHS 160D (Greyed-yellow). Pollen: Amount: Low. Color: RHS 155A (White).

*Fertile flower*.—Stamens: Number: Average: 10. Filament length: Average: 0.4 cm. Filament color: RHS NN155D (White). Anthers: Shape: Short oblong. Length: Average: 0.1 cm. Color: Lighter than RHS 160D (Greyed-yellow). Pollen: Amount: Low. Color: RHS 155A (White).

*Pistil*.—Number: Average: 3. Length: Average: 0.15 cm.

*Style*.—Length: Average: 0.1 cm. Color: RHS 157C (Green-white).

*Stigma*.—Shape: Club-shaped. Color: RHS 157B (Green-white).

*Ovary*.—Color: RHS 145D (Yellow-green).

Fruits/seeds: No fruits or seeds observed to date.

Disease and pest resistance: Similar to other varieties, no significant susceptibility for any disease.

COMPARISON WITH PARENTAL VARIETIES

Differences between the female parental line *Hydrangea paniculata* 'Grandiflora' and the 'Coubell' variety are described in Table 1 below.

TABLE 1

Comparison to Female Parent

| Characteristic | 'Coubell' | Female parent (unpatented) |
|---|---|---|
| Flower color | White | White with pinkish hue |
| Flower shape | Less conical than Female Parent | More conical than 'Coubell' |

COMPARISON TO KNOWN VARIETY

'Coubell' is most similar to the commercial *Hydrangea* plant named 'Limelight' ((U.S. Plant Pat. No. 12,874). Differences between the two varieties are described in Table 2 below.

TABLE 2

Comparison with Similar Variety

| Characteristic | 'Coubell' | Commercial line 'Limelight' (U.S. Plant Pat. No. PP12,874) |
|---|---|---|
| Flower shape | Less conical than 'Limelight' | More conical than 'Limelight' |
| Flower color | White | White with greenish hue |
| Leaf color | Darker green than 'Limelight' | Lighter green than 'Coubell' |

I claim:

1. A new and distinct variety of *Hydrangea* plant named 'Coubell' as shown and described herein.

* * * * *